(12) United States Patent
Hee

(10) Patent No.: US 6,215,639 B1
(45) Date of Patent: Apr. 10, 2001

(54) ADJUSTABLE, ELECTRICALLY CONDUCTIVE BRACELET

(76) Inventor: Roland Hee, 201 Bougainvilla Street, Ayala Alabang Village, Muntinlupa, 1780 (PH)

(*) Notice: Subject to any disclaimer, the term of this patent is extended or adjusted under 35 U.S.C. 154(b) by 0 days.

(21) Appl. No.: 09/389,717

(22) Filed: Sep. 3, 1999

(51) Int. Cl.$^7$ ................................................ H01H 47/00
(52) U.S. Cl. ................................. 361/212; 361/220
(58) Field of Search ......................... 361/212, 220, 361/223–224; 439/37; 57/901

(56) References Cited

U.S. PATENT DOCUMENTS

| | | |
|---|---|---|
| 1,531,862 | 3/1925 | Larned . |
| 2,586,747 | 2/1952 | Van Atta et al. .................. 175/264 |
| 2,928,100 | 3/1960 | Gagnon ................................. 2/339 |
| 2,955,234 | 10/1960 | Price ..................................... 317/2 |
| 2,998,697 | 9/1961 | Augenstein ............................ 59/80 |
| 3,063,447 | 11/1962 | Kirsten ............................... 128/134 |
| 3,237,395 | 3/1966 | Bennett . |
| 3,377,509 | 4/1968 | Legge ..................................... 317/2 |
| 3,422,460 | 1/1969 | Burke et al. ............................. 2/73 |
| 3,424,693 | 1/1969 | Lupinski et al. .................... 252/500 |
| 3,459,997 | 8/1969 | Legge ..................................... 317/2 |
| 3,541,389 | 11/1970 | Van Name ............................. 317/2 |
| 3,582,448 | 6/1971 | Okuhashi et al. .................... 161/87 |
| 3,596,134 | 7/1971 | Burke ................................. 317/2 B |
| 3,699,590 | 10/1972 | Webber et al. .......................... 2/73 |
| 3,810,258 | 5/1974 | Mathauser ........................ 339/12 R |
| 3,812,861 | 5/1974 | Peters ................................. 128/418 |
| 3,832,841 | 9/1974 | Cole ..................................... 57/152 |
| 3,851,456 | 12/1974 | Hamada et al. ................ 57/140 BY |
| 3,857,397 | 12/1974 | Brosseau ............................ 128/384 |
| 3,904,929 | 9/1975 | Kanaya et al. .................... 317/2 R |
| 3,949,129 | 4/1976 | Hubbard ............................. 428/190 |
| 3,986,530 | 10/1976 | Maekawa ......................... 139/425 R |
| 3,987,613 | 10/1976 | Woods et al. .................. 57/140 BY |
| 4,025,964 | 5/1977 | Owens ..................................... 3/1 |
| 4,112,941 | 9/1978 | Larimore ......................... 128/2.06 E |
| 4,211,456 | 7/1980 | Sears ................................. 339/12 R |
| 4,267,233 | 5/1981 | Tanaka et al. ...................... 428/389 |
| 4,321,789 | 3/1982 | Dammann et al. ................... 57/224 |
| 4,373,175 | 2/1983 | Mykkanen .......................... 361/220 |
| 4,398,277 | 8/1983 | Christiansen ....................... 361/220 |
| 4,402,560 | 9/1983 | Swainbank ........................... 339/11 |
| 4,420,529 | 12/1983 | Westhead ............................ 428/244 |
| 4,422,483 | 12/1983 | Zins ................................. 139/420 R |

(List continued on next page.)

FOREIGN PATENT DOCUMENTS

| | | |
|---|---|---|
| 3622948 | 1/1988 | (DE) . |
| 791199 | 2/1958 | (GB) . |
| 1067260 | 5/1967 | (GB) . |

OTHER PUBLICATIONS

"Magnetic Ground Strap Connector", Technical Digest, No. 76, Mar. 1985, p. 21.

ESD Control Products, "Trustat" Footware and Grounding Accessories, SIMCO, p. 39 and "Trustat" Conductive Wrist Straps and Ground Leads, p. 40 (No Date).

Westek Electrostatics, "Leg and Shoe Grounders", p. 8 and Personnel Grounding, p. 7 (No Date).

*Primary Examiner*—Michael J. Sherry
(74) *Attorney, Agent, or Firm*—Stetina Brunda Garred & Brucker

(57) ABSTRACT

An adjustable, electrically conductive bracelet extensible about a user's limb and adapted to prevent inadvertent contact with a source of electrical potential. The buckle system has a lower aperture configured for the endpiece to be insertable therethrough such that the inserted endpiece is disposed between the inner surface of the bracelet and the limb. In addition, the buckle system further has a strap puller to facilitate adjustments of the bracelet to form a plurality of alternate sizes.

11 Claims, 3 Drawing Sheets

U.S. PATENT DOCUMENTS

| | | | |
|---|---|---|---|
| 4,453,294 | 6/1984 | Morita | 24/303 |
| 4,459,633 | 7/1984 | Vandermark | 361/220 |
| 4,475,141 | 10/1984 | Antonevich | 361/220 |
| 4,551,783 | 11/1985 | Cohen et al. | 361/223 |
| 4,577,256 | 3/1986 | Breidegam | 361/220 |
| 4,639,825 | 1/1987 | Breidegam | 361/212 |
| 4,676,561 | 6/1987 | Barrett, II | 439/37 |
| 4,677,521 | 6/1987 | Frazier | 361/220 |
| 4,782,425 * | 11/1988 | Breidegam | 361/212 |
| 4,816,964 * | 3/1989 | Weiss | 361/220 |
| 4,847,729 | 7/1989 | Hee | 361/220 |
| 4,878,148 | 10/1989 | Hee | 361/220 |
| 5,004,425 | 4/1991 | Hee | 439/37 |
| 5,036,423 | 7/1991 | Williams | 361/212 |
| 5,184,274 * | 2/1993 | Weiss | 361/220 |
| 5,184,275 | 2/1993 | Wiegel et al. | 361/223 |
| 5,191,505 | 3/1993 | Gordon et al. | 361/223 |
| 5,576,924 | 11/1996 | Hee | 361/223 |
| 5,686,897 * | 11/1997 | Loh | 340/649 |

\* cited by examiner

ADJUSTABLE, ELECTRICALLY CONDUCTIVE BRACELET

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention generally relates to a buckle system for an electrically conductive bracelet, and more particularly to an improved buckle system that prevents a dangling endpiece of the bracelet from inadvertently contacting a source of electrical potential.

Buckle systems for electrically conductive bracelets are well known and in wide use throughout the electronics industry as well as other industries. During the assembly of electrical equipment, considerable difficulties may be encountered because components such as integrated circuits, for instance, may be disabled or destroyed by over-voltage or power density resulting from static electricity. Certain junctions in such circuits can be destroyed by as little as 50-volt potential, which radically changes the doping structure in their lattices.

A person walking on a carpet on a dry day can accumulate as much as 30,000 volts of potential, and can electrically generate thousands of volts by simply changing position in a chair or handling a styrofoam cup. Such a person can unintentionally discharge static electric potential into a circuit or component by touching it and causing over-voltage or excessive power density.

More and more frequently, personnel in industries, in which integrated circuits and other microelectronic components are handled or assembled, are taking measures to limit the failure rate of those circuits and components by attempting to keep both themselves and their environment at a zero electrical potential. Such measures include providing workers and work stations with anti-static carpet, conductive or dissipative grounded desk top work surfaces, hot air ion generators which emit ions to neutralize static charges, and electrically conductive bracelets worn by workers to keep workers at a zero potential.

Electrically conductive bracelets proved to be effective in keeping workers at a zero potential, especially when used with other anti-static measures as specified above. A manufacturer typically must depend upon the effectiveness of these bracelets to maintain a lower failure rate of such electronic circuits and components.

Electrically conductive bracelets should be electrically insulating on their exterior surfaces in order to reduce the hazard to a user from inadvertent contact of the bracelets surface with a source of electrical potential. The interior circumferential surface of the bracelet is intentionally made to be an excellent electrical conductor and in contact with the user. If the bracelets outer surface were to be conductive, and were in electrical contact with the inner circumferential surface, then a hazardous path of electrical current conduction to the body might be presented.

Accordingly, these considerations of selective conductivity have been recognized, and have been addressed by several types of electrically conductive bracelets, as disclosed and described in U.S. Pat. No. 4,878,148 to Hee, entitled CROCHETED FABRIC ELASTIC WRIST BRACELET BEARING AN INTERIOR CONDUCTIVE YARN, the teachings of which are incorporated herein by reference.

However, although the electrically conductive bracelets continued to improve, the mechanisms employed to secure these bracelets to a user have not. The electrically conductive bracelets in the above incorporated patent use a buckle that adjoins the two ends of the bracelet. More specifically, one end is inserted through the buckle to protrude outward through an aperture away from the user. As a result, this particular end is left dangling from the bracelet. The dangling end may be lengthy, depending on the limb size of the user.

These dangling ends have no useful purpose whatsoever, but rather subject the user to dangers that can be prevented with the application of the present invention. If the end is left to dangle freely, the risk of catching the same an a piece of electrical equipment is substantially increased. Electrocution is a possibility when the dangling end is accidentally caught in the electrical equipment, especially if the equipment is not grounded properly.

The dangling end may further subject the user to additional dangers in a chemical environment integrated to the above setting. The dangling end may contact a chemical that can be irritable to the skin, or even possibly toxic. The user may not be aware of the whereabouts of the dangling end since it is not a fixture that is closely contiguous to his body. Therefore, along with the possibility of electrocution, the user may be subjected to chemical poisoning as well.

In order to mitigate the above dangers, the users have frequently resorted to hiding the dangling end by tugging it into the bracelet. However, as stated previously, the material for the bracelet needs to be made with a highly conductive material. Therefore, tugging the dangling end into the bracelet tends to cut off at least a portion of the conductive contact between the bracelet and the user, thereby compromising the effectiveness of the bracelet for user safety.

Moreover, the users have also tried to alleviate the dangers by simply cutting off the dangling end. However, this method is also unsound because not only does it considerably decrease the effectiveness of the bracelet, the bracelet tend to deteriorate as well. More specifically, the materials for the bracelet tend to run, especially if the bracelets are composed of fabric as specified in the above incorporated patent.

Thus, there has long been a need in the industry, and in the microelectronics business in particular, for a method and an apparatus for preventing the dangling end of the bracelet from exposing the user to the above-described dangers. In particular, there is a need for a mechanism to affix the electrically conductive bracelet to the user without having the end dangerously dangling away from the bracelet, while simultaneously posing minimum inconvenience to the user by being easily adjustable to alternate sizes of the limb.

The present invention addresses and overcomes the above-described deficiency of prior art electrically conductive bracelets by providing a buckle system that is configured to place the end underneath the bracelet, rather than having the end dangling freely. Moreover, the bracelet is simultaneously user-friendly by having the end further attached to a strap puller for ease of adjustment. In this respect, not only does the present invention significantly reduce the risk of danger, but may also increase user comfort to provide minimum temptation to remove the bracelet to cause unintended damage to the workpiece.

BRIEF SUMMARY OF THE INVENTION

In accordance with a preferred embodiment of the present invention, there is provided an adjustable buckle system for preventing a dangling endpiece of an electrically conducting bracelet affixed around a persons limb from inadvertently contacting a source of electrical potential. The adjustable buckle system of the preferred embodiment comprises a grounding strap having a first end and a second end configured to slidably engage each other to form a plurality of alternate sizes.

Connected to the first end of the strap is an electrically insulating buckle. The electrically insulating buckle is further configured to secure the bracelet in one of the plurality of alternate sizes. In addition, a strap puller is attached to the second end of the grounding strap. More specifically, the strap second end is sewn to the strap puller. The puller is further configured to slidably engage the strap to facilitate adjustments of the bracelet to form the plurality of alternate sizes.

In accordance with a preferred embodiment of the present invention, the grounding strap is a crocheted fabric elastic grounding strap. Moreover, the grounding strap further comprises an inner surface and an outer surface. The strap inner surface is disposed circumferentially toward the limb, whereas the strap outer surface is disposed circumferentially away from the limb. The strap inner surface is further defined to be electrically conductive, while the strap outer surface is further defined to be electrically insulative.

In the preferred embodiment, the buckle further comprises a buckle slot configured for the strap second end to be insertable therethrough. Moreover, the buckle further comprises a lower aperture. The buckle lower aperture is configured for the strap second end to be insertable therethrough such that the strap second end is disposed between the inner surface of the strap and the limb. In addition, the buckle further comprises a buckle lock configured to secure the strap in one of the plurality of alternate sizes.

The buckle of the preferred embodiment further comprises an electrical snap operative to connect to a grounding source. More specifically, a grounding cord connects the electrical snap to the grounding source.

In accordance with a preferred embodiment of the present invention, the buckle system further comprises a method of utilizing the system defined by a strap puller and a buckle having a buckle slot, a buckle lock, and a lower aperture, for a grounding strap having a first end, a second end, an inner surface, and an outer surface. The preferred embodiment comprises the method of attaching the first end of the grounding strap to the buckle. Then, inserting the second end of the grounding strap through the buckle slot.

The method further comprises inserting the strap second end through the lower aperture of the buckle such that the strap second end is slidably contiguous to the inner surface of the strap. Next, attaching the strap second end to the strap puller. Moreover, the method further comprises slidably engaging the strap puller to the grounding strap such that the puller is adjustable along the strap to form a plurality of alternate sizes. Finally, securing the grounding strap in one of the plurality of alternate sizes with the buckle lock.

BRIEF DESCRIPTION OF THE DRAWINGS

These as well as other features of the present invention, will become more apparent upon reference to the drawings wherein.

DETAILED DESCRIPTION OF THE INVENTION

Figure 1:
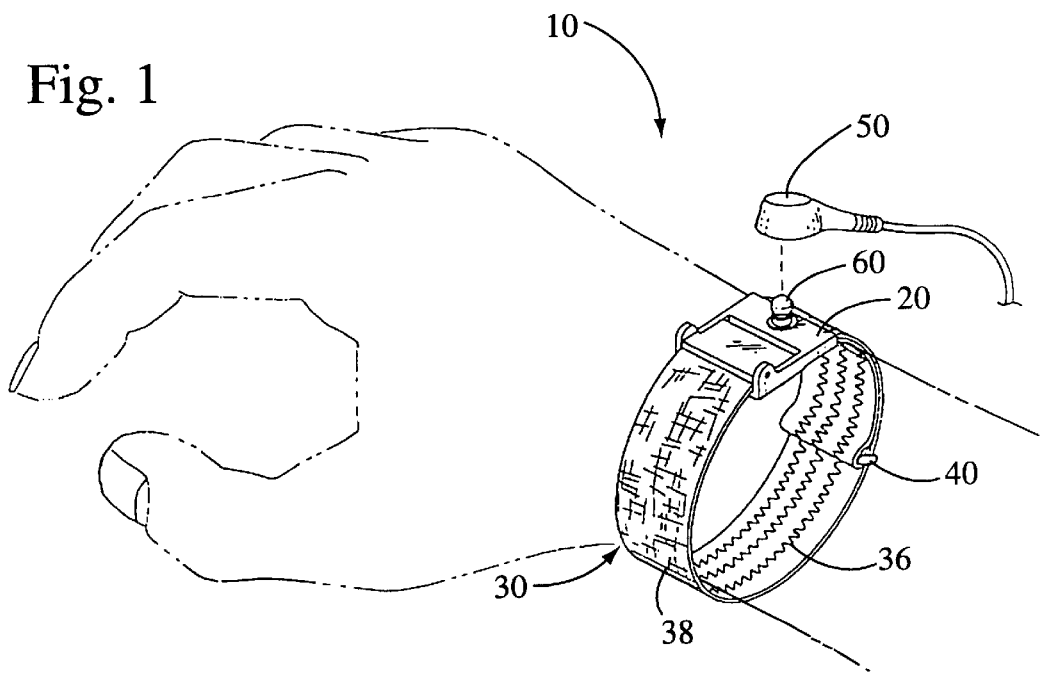
FIG. 1 is a perspective view of an electrically conductive bracelet with an adjustable buckle system constructed in accordance with a preferred embodiment of the present invention and including a strap puller attached to the bracelet.

Referring now to the drawings wherein the showings are for purposes of illustrating preferred embodiments of the present invention only, and not for purposes of limiting the same, FIG. 1 perspectively illustrates an electrically conductive bracelet 10 with an electrically insulating buckle 20 constructed in accordance with a preferred embodiment of the present invention. The bracelet 10 includes a grounding strap 30 attached to a strap puller 40 and the buckle 20.

Figure 2:
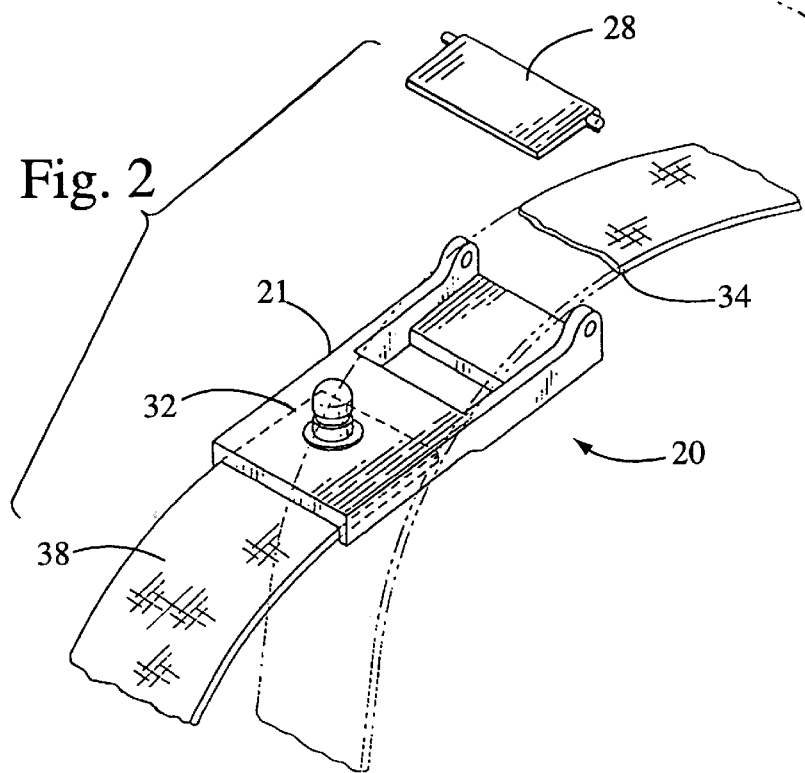
FIG. 2 is an exploded view of the buckle system shown in FIG. 1.

Referring now to FIGS. 1 and 2, the grounding strap 30 comprises a first end 32 and a second end 34. In addition, the grounding strap 30 is further defined by an inner surface 36 and an outer surface 38.

As specified in the incorporated U.S. Pat. No. 4,878,148, cited above, the inner surface of the grounding strap 36 is disposed circumferentially toward the limb. In addition, the inner surface 36 is intentionally made to be an excellent electrical conductor and to be in abutting contact with the limb. The conductive inner surface of the strap 36 is electrically connected to a grounding cord 50, which leads from the strap 30 to a grounding source.

Furthermore, the outer surface of the grounding strap 38 is disposed circumferentially away from the limb. The outer surface 38 is electrically insulating (at least in all areas wherein electrical connection is not intentionally made for the wicking of electrical charge to ground) in order that the hazard to a user from inadvertent contact of the outer surface 38 with a source of electrical potential should be reduced. If the outer surface of the grounding strap 38 were to be conductive, and were in electrical contact with the inner surface of the strap 36, then a hazardous path of electrical current conduction to the user might be presented. Furthermore, if the outer surface 38 were to catch or snag on the source of electrical potential, then the user may be detrimentally placed in contact with this source.

The grounding strap 30, as described above, may be any type of grounding strap to drain or wick static electrical charge from the user, as disclosed in the incorporated U.S. Pat. No. 4,878,148. However, a crocheted fabric elastic grounding strap is preferred because of its stretchable elastic materials.

Figure 3:
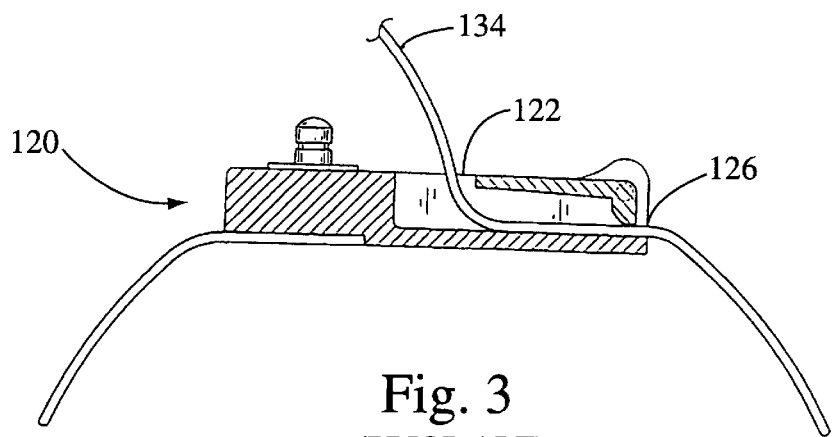
FIG. 3 is a side elevational view of a prior art buckle system for electrically conductive bracelets.
Figure 4:
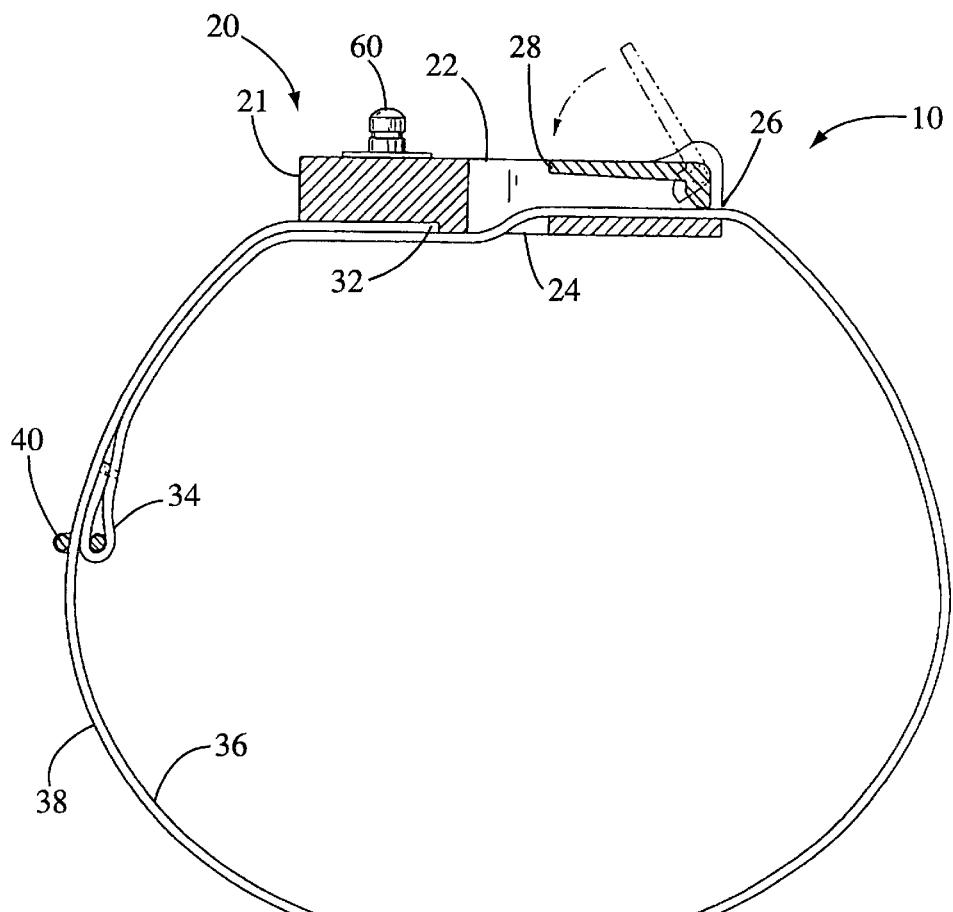
FIG. 4 is a side elevational view of the electrically conductive bracelet with the adjustable buckle system shown in FIG. 1.

Referring now to FIGS. 3 and 4, the electrically insulating buckle 20 is attached to the first end 32 of the grounding strap 30. As shown in these Figures, the buckle 20 of the present invention comprises an upper aperture 22 and a lower aperture 24, as opposed to the prior art buckle 120 only having an upper aperture 122. As stated, the prior art buckle 120 has the upper aperture 122 configured for the second end 134 of the grounding strap to be insertable therethrough. More specifically, the second end 134 is inserted through the buckle slot of the prior art buckle 126 to engage the upper aperture 122. The second end 134 goes through the upper aperture 122 to consequentially protrude outwards away from the user. As a result, the second end 134 is left to dangle freely to subject the user to potential dangers as specified above.

However, the buckle 20 of the present invention resolves this deficiency of the prior art buckle 120. As well as having the upper aperture 22, the buckle 20 further has the lower aperture 24. In particular, a buckle housing 21 defines the lower aperture 24. The lower aperture 24 of the buckle 20 is configured for the second end 34 of the grounding strap 30 to be insertable therethrough. More specifically, the second end 34 is inserted through a buckle slot 26 and through the lower aperture 24, rather than being advanced through the upper aperture 22 as disclosed in the prior art buckle 120. The second end 34 is pulled underneath the buckle 20 by going through the lower aperture 24. Consequently, the second end 34 of the grounding strap 30 is disposed between the inner surface 36 of the grounding strap 30 and the limb. In other words, the second end 34 is disposed between the electrically conductive inner surface 36 of the grounding strap 30 and the limb. Therefore, the second end 34 of the grounding strap 30 is simultaneously contiguous to both the inner surface 36 and the limb.

Pivotally attached to the buckle housing 21 is a buckle lock 28. The buckle lock 21 is movable between a locked position and an unlocked position. The buckle lock 28 is configured to secure the grounding strap 30 that has been inserted through the buckle slot 26 as specified above. The buckle lock 28 secures the grounding strap 30 in a plurality of alternate sizes as the grounding strap 30 is adjusted according to the limb size of the user. After the right size is determined, the user simply pushes the buckle lock 28 down to anchor the grounding strap 30 in place.

An electrical snap 60 is mounted centrally within the electrically insulating buckle 20. The electrical snap 60 connects the inner surface 36 of the grounding strap 30 to the grounding cord 50. The grounding cord 50 normally snaps to the electrical snap 60 and contains a one megaohm resistor to prevent electrocution if it were to inadvertently contact the source of electrical potential. Moreover, the grounding cord 50 is further connected to the grounding source, and is the path by which electrostatic charges are wicked from the user to ground.

Figure 5:
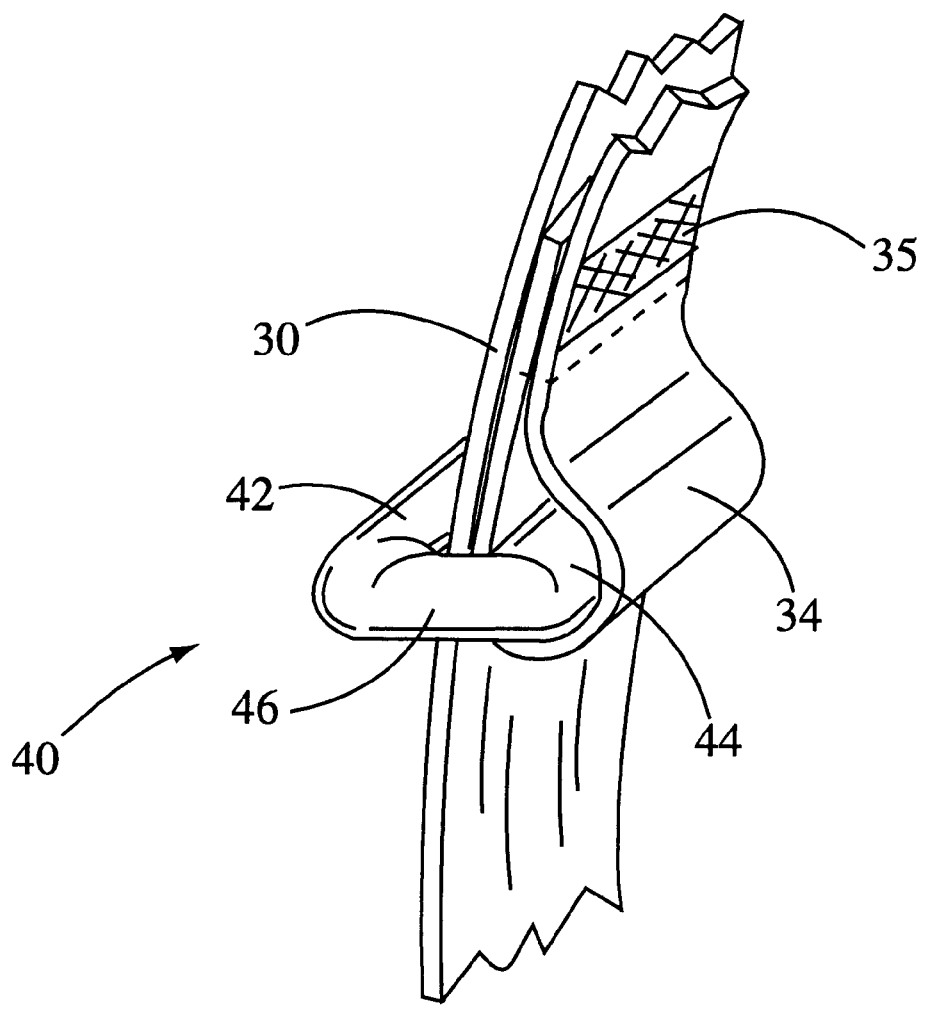
FIG. 5 is an exploded view of the strap puller shown in FIG. 1.

Referring now to FIG. 5, in accordance with the preferred embodiment of the present invention, the electrically conductive bracelet 10 further comprises the strap puller 40. As stated above, the second end 34 of the grounding strap 30 is disposed between the inner surface 36 and the limb, with the second end 34 being used to facilitate adjustments of the bracelet 10 to form the plurality of alternate sizes. More specifically, the strap puller 40 is attached to the second end 34 of the grounding strap 30, while simultaneously engaging the grounding strap 30 to be slidably movable therealong.

The strap puller 40 may be any type of puller to facilitate the adjustment of the bracelet 10. However, the preferred puller 40 is shown in FIG. 5. In particular, the illustrated puller 40 has a first cylindrical piece 42 and a second cylindrical piece 44 which extend in spaced, generally parallel relation to each other. Rod connectors 46 hold the two parallelly positioned cylindrical pieces 42, 44 together by attaching to their corresponding ends, leaving a space between the two pieces.

The second end 34 of the grounding strap 30 is attached to the second cylindrical piece 44. More specifically, the second end 34 loops around the second cylindrical piece 44 and is sewn, or even hot sealed, to the second end portion 35. In addition, the grounding strap 30 is loosely placed between the two cylindrical pieces 42, 44. Thus, the puller 40 assists in pulling the attached second end 34 along the inner surface 36 to tighten the grounding strap 30 according to the user's limb size before the buckle lock 28 is used to secure it in place.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. An adjustable, electrically conductive bracelet extensible about a user's limb and adapted to prevent inadvertent contact with a source of electrical potential, the bracelet comprising:

an elongate grounding strap having a first end, a second end, and an electrically conductive inner surface which contacts the user's limb when the bracelet is extended thereabout; and an electrically insulating buckle attached to the first end, the buckle having a lower aperture which is juxtaposed to the user's limb when the bracelet is extended thereabout, the second end being advanceable through the lower aperture so as to be disposed between the inner surface of the strap and the limb.

2. The bracelet as set forth in claim 1 wherein the grounding strap further comprises an electrically insulative outer surface.

3. The bracelet as set forth in claim 1 wherein the grounding strap is fabricated from a crocheted fabric elastic material.

4. The bracelet as set forth in claim 1 further comprising a strap puller attached to the strap in close proximity to the second end thereof, the strap puller further being configured to slidably engage the strap to facilitate adjustments of the bracelet to alternate sizes.

5. The bracelet as set forth in claim 1 wherein the buckle comprises:

a buckle housing which defines the lower aperture; and a buckle lock pivotally connected to the buckle housing and movable between a locked position whereat the strap is maintained in fixed relation to the buckle housing and an unlocked position whereat the strap is slidably movable relative to the buckle housing.

6. The bracelet as set forth in claim 5 wherein the buckle housing and the buckle lock collectively define a buckle slot, the second end of the strap being advanceable through the buckle slot prior to being advanced through the lower aperture.

7. The bracelet as set forth in claim 5 wherein the buckle further comprises an electrical snap attached to the buckle housing and connectable to a grounding source.

8. A method of securing an adjustable, electrically conductive bracelet to a user's limb, the bracelet including an electrically insulating buckle having a lower aperture, and a grounding strap including a first end attached to the buckle, a second end, and an inner surface, the method comprising the steps of:

wrapping the grounding strap about the user's limb; and advancing the second end of the grounding strap through the lower aperture of the buckle such that the second end is contiguous to the inner surface of the strap.

9. The method of claim 8 wherein the bracelet further comprises a strap puller, the method further comprising the step of:
   attaching the strap puller to the strap in close proximity to the second end thereof.

10. The method of claim 9 further comprising the step of:
   slidably engaging the strap puller to the strap to facilitate adjustments of the bracelet to alternate sizes.

11. The method of claim 10 wherein the bracelet further comprises a buckle lock, the method further comprising the step of:
   securing the strap in one of the plurality of alternate sizes with the buckle lock.

* * * * *